United States Patent [19]
Parkin

[11] Patent Number: 5,228,436
[45] Date of Patent: Jul. 20, 1993

[54] PROXIMAL FLUID TRAP

[75] Inventor: Samuel C. Parkin, Houston, Tex.

[73] Assignee: Marvin Bein, Clear Lake Shores, Tex. ; a part interest

[21] Appl. No.: 928,308

[22] Filed: Aug. 12, 1992

[51] Int. Cl.⁵ .............................................. A62B 7/10
[52] U.S. Cl. ........................... 128/205.12; 128/204.18; 128/203.12
[58] Field of Search ............... 128/205.12, 203.12, 128/204.18, 204.16, 205.24

[56] References Cited

U.S. PATENT DOCUMENTS

| | | | |
|---|---|---|---|
| 2,822,808 | 2/1958 | Boone | 128/760 |
| 3,454,005 | 7/1969 | Eubanks et al. | 128/205.12 |
| 3,968,812 | 7/1976 | Eross | 128/205.12 |
| 4,391,271 | 7/1983 | Blanco | 128/205.12 |
| 4,417,574 | 11/1983 | Talonn et al. | 128/205.12 |
| 4,456,008 | 6/1984 | Clawson et al. | 128/205.12 |
| 4,457,305 | 7/1984 | Shanks et al. | 128/205.12 |
| 4,867,153 | 9/1989 | Lorenzen et al. | 128/205.12 |

Primary Examiner—Edgar S. Burr
Assistant Examiner—Aaron J. Lewis
Attorney, Agent, or Firm—Nies, Kurz, Bergert & Tamburro

[57] ABSTRACT

A device for trapping condensation such as condensed water vapor and moisture from a gas directing tube in a single piece unit is disclosed. The device is particularly useful with respiratory therapy machines. The present invention allows condensation to travel in only one direction and includes at least one inlet pipe and at least one outlet pipe connected to the gas directing tube. A fluid reservoir is formed between the interior wall of the inlet pipe or pipes and the exterior wall of the extended internal portion of the outlet pipe or pipes. The external and internal portions of the device may be altered in shape and size for use in different applications.

8 Claims, 2 Drawing Sheets

PROXIMAL FLUID TRAP

BACKGROUND AND SUMMARY OF THE INVENTION

When using volume ventilators or other respiratory therapy machines while administering respiratory therapy, a ventilator circuit which employs flexible corrugated tubing is usually employed to connect the patient to the machine. Since heaters and humidifiers are often used with this type of equipment, condensation of water vapor and moisture along the interior walls of the tubing occurs due to the high levels of humidity in the gaseous mixture. The greatest amounts of condensation will usually form where the gas is at its highest temperature in the tubes. This occurs frequently when the warm humid gaseous mixture enters the inspiratory tube of the circuit from the ventilator-humidifier and when the patient exhales air into the expiratory tube of the circuit.

Previous devices for use in fluid collection are described, for example, in the following U.S. Pat. Nos.: 2,822,808 to Boone, 3,454,005 to Eubanks et al; 3,968,812 to Eross; 4,391,271 to Blanco; 4,417,574 to Talonn et al; 4,456,008 to Clawson et al; and 4,457,305 to Shanks et al.

Water drains or traps are commonly used to collect and remove the objectionable condensation from ventilator circuits so that condensed moisture in excessive amounts cannot reach the patient. To function properly these traps are inserted in the circuit at a point of relatively low elevation so that the condensed liquid will flow by gravity into the drain or trap.

These drains or water traps serve their intended purpose quite effectively to collect and remove the majority of the condensation from all but a short portion of the ventilator circuit. The section of tubing in the arcuate path between the patient and the tube hanger which is supported by the tube hanger support arm at a level which is considered relatively high, is normally a 1 comparatively short section of tubing. For the most part it is impractical to use existing water traps or drains in this short arcuate section of tubing and therefore the condensation problem in this portion of the equipment has not been resolved. This condensation is located so proximal to the patient that the least change in the arc of the circuit tube, i.e., patient movement or repositioning, can result in condensation being dumped into the patient airway. Such action causes great discomfort and possible choking to the patient and can introduce harmful bacteria which may lead to serious respiratory complications.

The proximal fluid trap of the present invention in this respiratory therapy application functions so as to prevent condensation which forms in the ventilator circuit tubing between the patient and the tube hanger from being dumped into the patient airway. It is a single piece unit with no moving or removable components other than optional ports found on standard ventilator circuit patient wye connectors, and includes (1) an inlet pipe to connect to the inspiration tubing, and/or an inlet pipe to connect to the exhalation tubing, (2) an outlet pipe to connect with the endotracheal or tracheostomy tube or patient elbow, or other device and (3) an internal fluid reservoir. The present invention is intended to replace the standard patient wye connector. The invention traps condensation in the collection reservoir without obstructing or altering the air supply to the patient. The advantages of such a device will be evident to those familiar with the art. The particular shapes and sizes of the proximal fluid trap of the present invention can be adapted to fit the application or needs and desires of the user without changing the distinct function of the invention.

DESCRIPTION OF THE PREFERRED EMBODIMENTS

Figure 2:
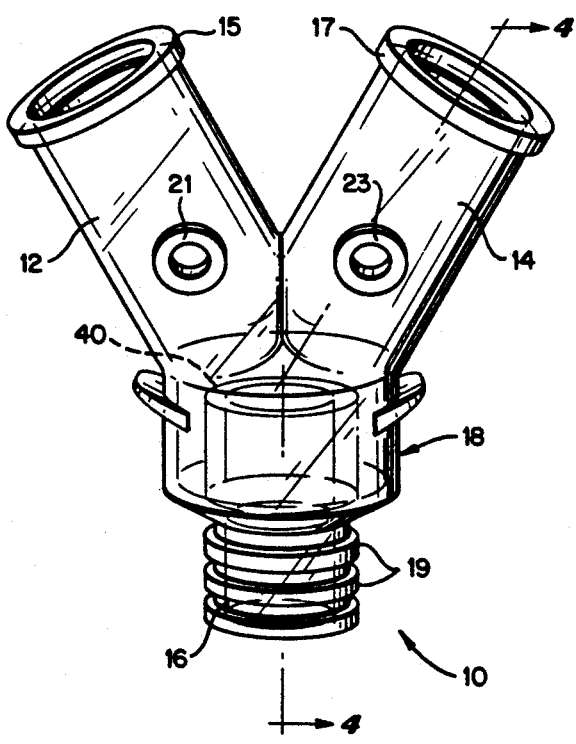
FIG. 2 is a perspective view of a first embodiment of the proximal fluid trap of the present invention.
Figure 3:
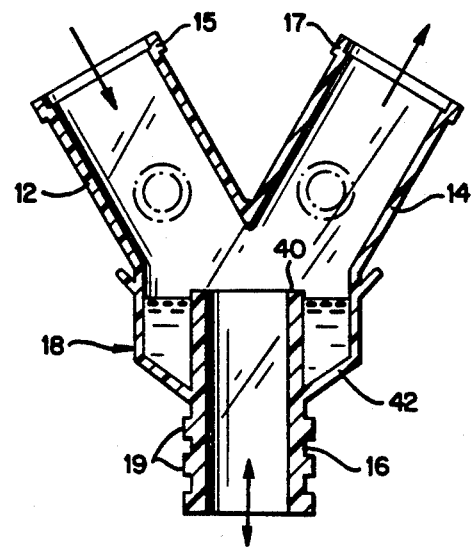
FIG. 3 is a front elevation in cross section of the proximal fluid trap of FIG. 2.
Figure 4:
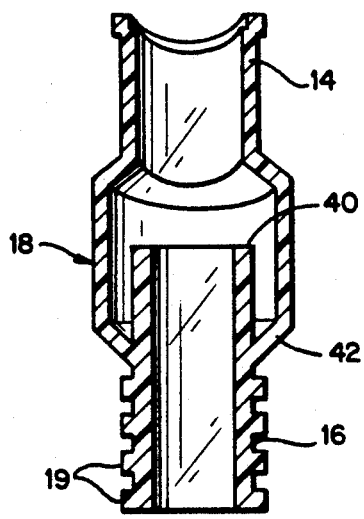
FIG. 4 is a cross section taken along line 4—4 of FIG. 2.

In the embodiment of the invention as shown in FIGS. 2 through 4, there is provided a proximal fluid trap 10 having inlet pipes 12 and 14, an outlet pipe 16 and an internal fluid reservoir 18. Either of the inlet pipes 12, 14 may be connected to the inspiration tubing with the other inlet pipe being connected to the exhalation tubing. The inlet pipes 12, 14 are provided with an outer flange 15, 17 for use in the connection of tubing. The outlet pipe 16 may be provided with ridges 19. Optional ports 21,23 may be provided in these or other locations for specific purposes and these may be opened or closed as needed.

Figure 1:
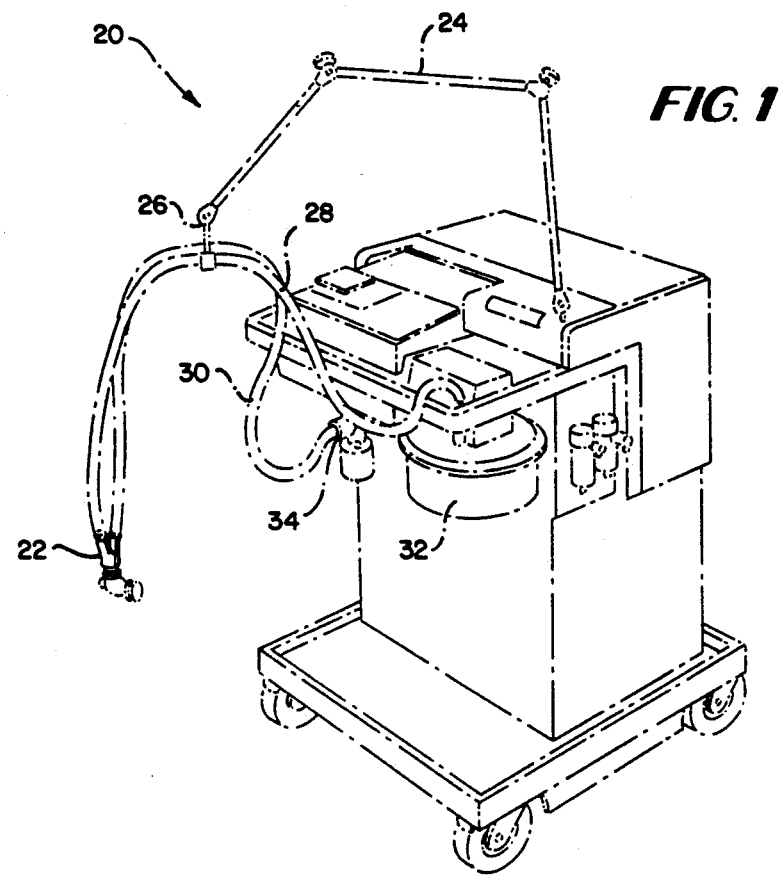
FIG. 1 is a perspective view of one example of a ventilator machine which may be employed with the present invention.

The fluid trap 10 of the present invention is advantageously employed with a ventilator 20 as shown in FIG. 1 with the fluid trap 10 being located in the patient tube Y-coupler or wye position 22 in FIG. 1 so as to be proximal to the patient. The ventilator 20 includes a ventilator tube hanger support arm 24 with attached tube hanger 26 which holds the inspiration tube segment 28 and the exhalation tube segment 30. The inspiration tube segment 28 is connected at its inner end to a source of air which passes through a humidifier 32. The exhalation tube segment 30 is connected at its inner end to an air exhaust after passing through an exhalation tube cuff connection 34.

As can be seen in FIGS. 3 and 4, the outlet pipe 16 of this embodiment has an inner extension 40 on the interior of the trap 10 which serves to provide the inner side walls for the fluid reservoir 18. The exterior side walls 42 of the reservoir 18 extend outwardly from the extension 40 a distance sufficient to provide the needed reservoir volume for retaining fluid. The inner extension 40 is preferably of the same diameter as the outlet pipe 16 and preferably aligned with the inlet pipes 12 and 14 as shown in FIG. 4. It is also within the scope of the present invention for this inner extension 40 to be of a larger or smaller relative diameter and for inner extension 40 to be offset relative to the inlet pipes 12 and 14. In this manner, the air flow to and from the patient remains unrestricted. The arrows in FIG. 3 depict the air flow.

As illustrated in FIGS. 2 through 4, the newly designed patient wye incorporating the proximal fluid trap 10 of the invention acts to collect liquids in the fluid reservoir 18. The liquids are prevented from entering the patient airway, and the air supply to the patient remains unrestricted.

Figure 5:
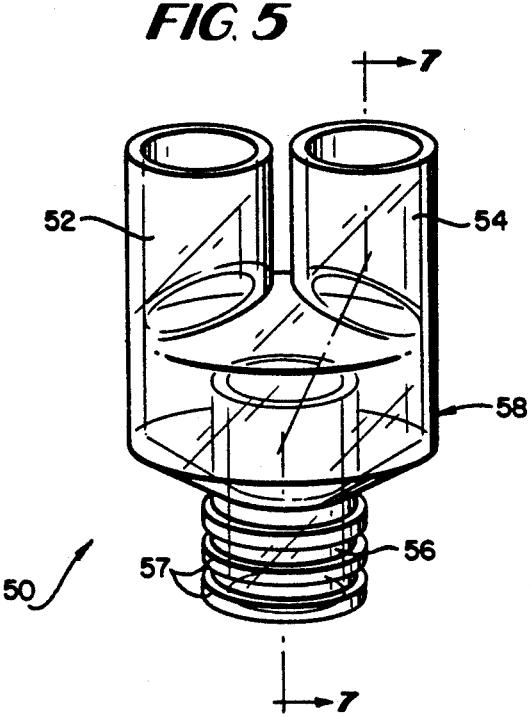
FIG. 5 is a perspective view of a second embodiment of the proximal fluid trap of the present invention.
Figure 6:
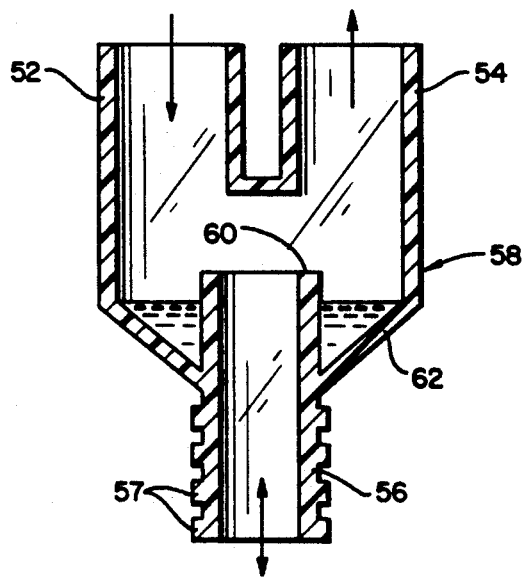
FIG. 6 is a front elevation in cross section of the proximal fluid trap of FIG. 5.
Figure 7:
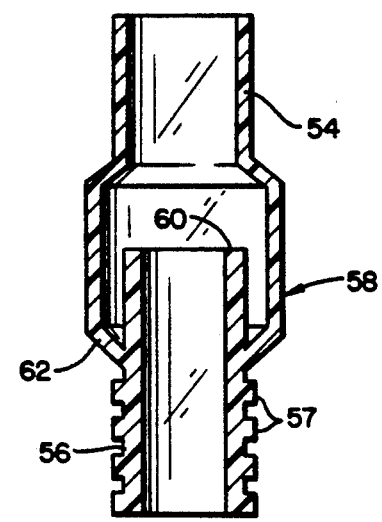
FIG. 7 is a cross section taken along line 7—7 of FIG. 5.

In the embodiment of FIGS. 5 through 7, the proximal fluid trap 50 has inlet pipes 52 and 54, an outlet pipe 56 and an internal fluid reservoir 58. Either of the inlet pipes 52, 54 may be connected to the inspiration tubing with the other inlet pipe being connected to the exhalation tubing. The outlet pipe 56 has an inner extension 60 on the interior of the trap 50 which serves to provide the inner side walls for the fluid reservoir 58. The exterior side walls 62 of the reservoir 58 extend outwardly from the extension 60 a distance sufficient to provide the needed reservoir volume for retaining fluid. The outlet pipe 56 may be provided with ridges 57.

The proximal fluid trap 50 is also generally employed with a ventilator such as that shown in FIG. 1.

In the embodiment of FIGS. 5 through 7, the air flow also remains unrestricted, with the arrows in FIG. 6 depicting air flow. As with the previous embodiment, the inner extension 60 is preferably of the same diameter as the outlet pipe 56 and preferably aligned with the inlet pipes 52 and 54 as shown in FIG. 7. It is also within the scope of the present invention for the inner extension 60 to be of a larger or smaller relative diameter and for inner extension 60 to be offset relative to the inlet pipes 52 and 54.

As with the previous embodiment, optional ports may be provided in the exterior walls of the device 50 in any desired position or location.

The following Table I shows a comparison of the respiratory therapy application of the proximal fluid trap of the present invention to other water trap products previously patented for respiratory therapy use:

TABLE I

| Proximal Fluid Trap | Prior Art Traps |
| --- | --- |
| Located in very close proximity to patient (connects to the endotracheal or tracheostomy tube) and prevents condensation spillage into the patient's respiratory system | Located at a point of relatively low elevation so that water condensation on the inner walls of the tubes will drain by gravity to the trap (usually placed about half-way between the patient and the ventilator) |
| Designed to prevent small amounts of condensed moisture not collected in the prior art traps (about 20 cc or less) from accidental spillage into the patient's respiratory system | Designed to remove condensed moisture from a breathing tube so only small amounts of condensation can reach the patient's respiratory system |
| Designed as a single piece unit with no moving or removable components other than standard ports usually found on standard patient wye connectors (in this application it will replace the standard patient wye connector) | Designed as a condensation collection and/or removal system with different moving, removable or electrical components (not related to the patient wye connector in any way) |
| Designed to be used in conjunction with the present water removal systems, not to compete with them in any fashion. They perform entirely different tasks in the same ventilator circuit system | Each different patented water trap assembly was designed as an improvement over previous designs. Each was intended to compete as the best product design available. They all performed the same task |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A device in the form of a single piece unit for trapping condensation such as condensed water vapor and moisture from a gas directing tube to prevent the condensation from moving in one direction but allowing said condensation to freely move in the opposite direction, comprising:

a housing defining a chamber having exterior side walls;

at least one inlet pipe in said housing opening to said chamber; and at least one outlet pipe in said housing opening to said chamber, said outlet pipe having an inner extension which intersects said exterior side walls of the chamber and projects inwardly into said chamber to an inner end, with said inwardly projecting, inner extension having a wall which is continuous and fluid tight from said inner end to its intersection with the exterior side walls of the chamber, thereby forming a fluid reservoir between the exterior side walls of the chamber and the inner extension of the outlet pipe;

said inner extension of the outlet pipe defining an airway having a smooth inner surface with no lip or other radially inwardly extending protrusion which would restrict the free flow of gas through said outlet pipe.

2. The device of claim 1 wherein the inner extension of the outlet pipe has substantially the same diameter as the outlet pipe and wherein the inner extension is aligned with the inlet pipe so as to contribute to unrestricted air flow.

3. The device of claim 1 having two inlet pipes in a U-shaped configuration.

4. The device of claim 1 having two inlet pipes in a Y-shaped configuration.

5. A method for trapping condensation from a gas directing tube between a patient and a respiratory machine connected by gas directing tube means to a patient tube proximal to a patient, said method comprising:

(a) providing a housing defining a chamber having exterior side walls in the position of the patient tube proximal to the patient;

(b) providing at least one inlet pipe in said housing opening to said chamber; and (c) providing at least one outlet pipe in said housing opening to said chamber, said outlet pipe having an inner extension which intersects said exterior side walls of the chamber and projects inwardly into said chamber to an inner end, with said inwardly projecting, inner extension having a wall which is continuous and fluid tight from said inner end to its intersection with the exterior side walls of the chamber, thereby forming a fluid reservoir between the exterior side walls of the chamber and the inner extension of the outlet pipe, said inner extension of the outlet pipe defining an airway having a smooth inner surface with no lip or other radially inwardly extending protrusion which would restrict the free flow of gas through said outlet pipe.

6. The method of claim 5 which further includes providing the inner extension of the outlet pipe with substantially the same diameter as the outlet pipe and wherein the inner extension is aligned with the inlet pipe so as to contribute to unrestricted air flow.

7. The method of claim 5 which further includes providing two inlet pipes in a U-shaped configuration.

8. The method of claim 5 which further includes providing two inlet pipes in a Y-shaped configuration.

* * * * *